United States Patent
Mohr et al.

(10) Patent No.: US 10,600,510 B2
(45) Date of Patent: Mar. 24, 2020

(54) VIDEO CONTENT SEARCHES IN A MEDICAL CONTEXT

(71) Applicant: Intuitive Surgical Operations, Inc., Sunnyvale, CA (US)

(72) Inventors: Catherine J. Mohr, Mountain View, CA (US); Brian E. Miller, Los Gatos, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 151 days.

(21) Appl. No.: 15/735,073

(22) PCT Filed: Jun. 9, 2016

(86) PCT No.: PCT/US2016/036368
§ 371 (c)(1),
(2) Date: Dec. 8, 2017

(87) PCT Pub. No.: WO2016/200887
PCT Pub. Date: Dec. 15, 2016

(65) Prior Publication Data
US 2018/0322949 A1 Nov. 8, 2018

Related U.S. Application Data

(60) Provisional application No. 62/173,187, filed on Jun. 19, 2015.

(51) Int. Cl.
*G06K 9/00* (2006.01)
*G16H 30/40* (2018.01)
(Continued)

(52) U.S. Cl.
CPC ............ *G16H 30/40* (2018.01); *G06F 16/71* (2019.01); *G06T 7/0012* (2013.01); *G16H 30/20* (2018.01);
(Continued)

(58) Field of Classification Search
CPC ......... G06T 2207/10016; G06T 7/0012; G06T 2207/10068; G06T 2207/30004;
(Continued)

(56) References Cited

U.S. PATENT DOCUMENTS 7,623,709 B2   11/2009  Gering et al.
8,443,279 B1 *  5/2013  Hameed ............ A61B 1/00041
                                                715/230
(Continued)

FOREIGN PATENT DOCUMENTS

CA         2903088 A1     9/2014
WO   WO-2009045827 A2    4/2009

OTHER PUBLICATIONS

International Search Report and Written Opinion for Application No. PCT/US16/36368, dated Sep. 7, 2016, 12 pages.
(Continued)

*Primary Examiner* — Li Liu
(74) *Attorney, Agent, or Firm* — Schwegman Lundberg & Woessner, P.A.

(57) ABSTRACT

A method of searching video content for specific subject matter of interest augments traditional image data analysis methods with analysis of contemporaneously gathered non-image data. One application involves video recordings of medical procedures performed using a medical device. When a user desires to locate portions of video recordings showing a medical event of interest, one or more medical device system events likely to correspond to the occurrence of the medical event of interest are identified from one or more procedure event logs. Timestamps associated with these system events are used to identify candidate video clips from the procedure video recordings. Image data
(Continued)

analysis is performed on the candidate video clips to determine whether each candidate video clip contains the medical event of interest.

24 Claims, 10 Drawing Sheets

(51) Int. Cl.
*G06F 16/71* (2019.01)
*G16H 30/20* (2018.01)
*G16H 40/63* (2018.01)
*G06T 7/00* (2017.01)
*G06N 20/00* (2019.01)

(52) U.S. Cl.
CPC ............ *G16H 40/63* (2018.01); *G06N 20/00* (2019.01); *G06T 2207/10016* (2013.01); *G06T 2207/30004* (2013.01)

(58) Field of Classification Search
CPC ........... G06T 2207/20081; G06F 19/00; G06F 19/321; G06F 16/7867; G06F 16/71; G06F 16/78
See application file for complete search history.

(56) References Cited

U.S. PATENT DOCUMENTS

| | | | |
|---|---|---|---|
| 2002/0172498 A1* | 11/2002 | Esenyan | G11B 27/034 386/241 |
| 2010/0333194 A1* | 12/2010 | Ricordi | G06F 21/32 726/17 |
| 2011/0301447 A1* | 12/2011 | Park | G06T 7/0016 600/407 |
| 2012/0263430 A1 | 10/2012 | Spitzer-Williams | |
| 2012/0316421 A1 | 12/2012 | Kumar et al. | |
| 2014/0089803 A1 | 3/2014 | Weast et al. | |
| 2015/0035959 A1* | 2/2015 | Amble | A61B 8/565 348/74 |
| 2016/0067007 A1* | 3/2016 | Piron | A61B 5/7246 705/3 |
| 2018/0214139 A1* | 8/2018 | Yan | A61B 90/37 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Extended European Search Report for Application No. EP16808157. 8, dated Jan. 10, 2019, 9 pages.

* cited by examiner

| TIMESTAMP | EVENT CODE | DESCRIPTION |
|---|---|---|
| 2015 JAN. 1, 8:50 AM | 300000 | SYSTEM POWER ON |
| 2015 JAN. 1, 9:00 AM | 300001 | START VIDEO RECORDING |
| ⋮ | ⋮ | ⋮ |
| 2015 JAN. 1, 10:00 AM | 300005 | BIPOLAR CAUTERY FORCEPS INSTALLED |
| 2015 JAN. 1, 10:01 AM | 300006 | NEEDLE DRIVER INSTALLED |
| ⋮ | ⋮ | ⋮ |
| 2015 JAN. 1, 10:10 AM | 300010 | BIPOLAR CAUTERY FORCEPS REMOVED |
| ⋮ | ⋮ | ⋮ |
| 2015 JAN. 1, 11:00 AM | 300005 | BIPOLAR CAUTERY FORCEPS INSTALLED |
| 2015 JAN. 1, 11:05 AM | 300011 | NEEDLE DRIVER REMOVED |
| ⋮ | ⋮ | ⋮ |
| 2015 JAN. 1, 11:10 AM | 300010 | BIPOLAR CAUTERY FORCEPS REMOVED |
| ⋮ | ⋮ | ⋮ |
| 2015 JAN. 1, 12:00 PM | 300005 | BIPOLAR CAUTERY FORCEPS INSTALLED |
| 2015 JAN. 1, 12:01 PM | 300006 | NEEDLE DRIVER INSTALLED |
| ⋮ | ⋮ | ⋮ |
| 2015 JAN. 1, 12:10 PM | 300010 | BIPOLAR CAUTERY FORCEPS REMOVED |
| 2015 JAN. 1, 12:11 PM | 300011 | NEEDLE DRIVER REMOVED |
| 2015 JAN. 1, 1:00 PM | 300099 | SYSTEM POWER OFF |

*Fig. 8*

VIDEO CONTENT SEARCHES IN A MEDICAL CONTEXT

CROSS-REFERENCE TO RELATED APPLICATIONS

This application is a U.S. National Stage Filing under 35 U.S.C. 371 from International Application No. PCT/US2016/036368, filed on Jun. 8, 2016, and published as WO 2016/200887 A1 on Dec. 15, 2016, which claims the benefit of priority under 35 U.S.C. § 119(e) to U.S. Provisional Patent Application No. 62/173,187, filed on Jun. 9, 2015, each of which is hereby incorporated by reference herein in its entirety.

COPYRIGHT NOTICE

A portion of the disclosure of this patent document contains material which is subject to copyright protection. The copyright owner has no objection to the facsimile reproduction by any-one of the patent document or the patent disclosure, as it appears in the Patent and Trademark Office patent file or records, but otherwise reserves all copyright rights whatsoever.

BACKGROUND

1. Field of Invention

Inventive aspects generally relate to video content searching. In particular, they relate to the searching medical procedure video recordings for certain subject matter of interest, and the retrieval of video clips that show the subject matter of interest.

2. Art

It is desirable to have the ability to locate certain subject matter of interest in a video recording, without having knowledge of the precise point in the video recording at which the sought after subject matter is shown. Thus, it is desirable to have to have video search capabilities that enable a user to perform key word or key phrase subject matter searches of video recordings.

Subject matter searches of video recordings typically involve an algorithmic approach that relies exclusively on analysis of image data. See, for example U.S. Pat. No. 7,623,709 to Gering, entitled "Method and System for Segmenting Image Data". Generally speaking, analyses of image data try to identify certain patterns that exist among the various pixels of an image (e.g., a frame of a video) that are determined to be indicative of various subject matter of interest. Image characteristics used to perform these analyses may include patterns in pixel color, pixel intensity, lines or contours in the image formed by adjacent pixels, and the like. The subject matter of an image by analysis of image data is challenging and computationally intensive, an observation with which U.S. Pat. No. 7,623,709 agrees. Additionally, the results returned are often inaccurate.

In view of the limitations associated with determining the subject matter of an image exclusively using image data analysis, an improved system and method for performing subject matter searches of video recordings is desirable. In one aspect, a video recording is associated with various system events taking place on a medical system. Information about the system events taking place on the medical system provide an additional data set that may be indicative of certain events taking place in the video recording. When searching the recorded video for specific subject matter of interest, analysis of this additional data set can be used to augment image data analysis of the video recording. This search approach would be preferred over a search approach that relies exclusively on image data analysis if it can minimize the computational intensity of the search and improve the search accuracy.

SUMMARY

The following summary introduces certain aspects of the inventive subject matter in order to provide a basic understanding. This summary is not an extensive overview of the inventive subject matter, and it is not intended to identify key or critical elements or to delineate the scope of the inventive subject matter. Although this summary contains information that is relevant to various aspects and embodiments of the inventive subject matter, its sole purpose is to present some aspects and embodiments in a general form as a prelude to the more detailed description below.

A method of searching recorded video is disclosed. The method involves receiving a user command to locate one or more video clips showing a medical event of interest from one or more procedure video recordings. Next, one or more system events likely to correspond to the occurrence of the medical event of interest are identified from one or more procedure event logs. Using one or more timestamps corresponding to each of the one or more system events, one or more candidate video clips are identified from the one or more procedure video recordings. By performing an analysis of image data, a determination is made with regards to whether each of the one or more candidate video segments is an identified video segment that contains the medical event of interest. At least one identified video segment is presented to a user.

A computing device for performing a video search is disclosed. The computing device includes a user interface and a processing unit including one or more processors. The processing unit is operatively coupled to the user interface, and it is configured receive a user command to locate one or more video clips showing a medical event of interest from one or more procedure video recordings. The processing unit is further configured to identify from one or more procedure event logs one or more system events likely to correspond to the occurrence of the medical event of interest. Using one or more timestamps corresponding to each of the one or more system events, the processing unit is configured to identify one or more candidate video clips are from the one or more procedure video recordings. The processing unit performs an analysis of image data to determine whether each of the one or more candidate video segments is an identified video segment that contains the medical event of interest. The processing unit presents at least one identified video segment to a user, e.g., on a display.

BRIEF DESCRIPTION OF THE DRAWINGS

FIG. 8 is a diagram showing the data structure of an event log of a medical system.

DETAILED DESCRIPTION

Figure 1:
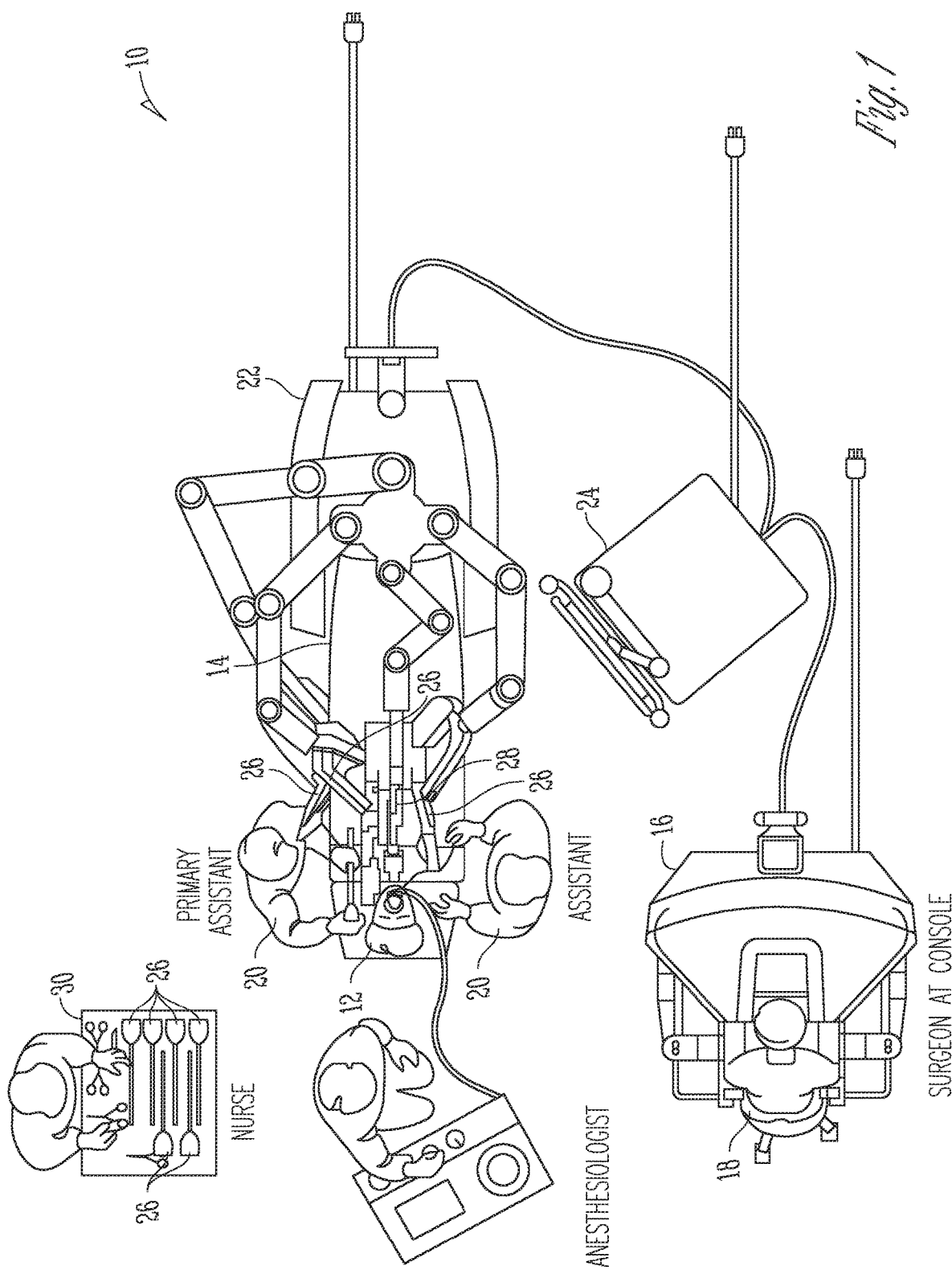
FIG. 1 is a plan view of a minimally invasive teleoperated surgical system.

This description and the accompanying drawings that illustrate inventive aspects, embodiments, implementations, or applications should not be taken as limiting—the claims define the protected invention. Various mechanical, compositional, structural, electrical, and operational changes may be made without departing from the spirit and scope of this description and the claims. In some instances, well-known circuits, structures, or techniques have not been shown or described in detail in order not to obscure the invention. Like numbers in two or more figures represent the same or similar elements.

Further, this description's terminology is not intended to limit the invention. For example, spatially relative terms— such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly. Likewise, descriptions of movement along and around various axes includes various special device positions and orientations. In addition, the singular forms "a", "an", and "the" are intended to include the plural forms as well, unless the context indicates otherwise. And, the terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

Elements described in detail with reference to one embodiment, implementation, or application may, whenever practical, be included in other embodiments, implementations, or applications in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, implementation, or application may be incorporated into other embodiments, implementations, or aspects unless specifically described otherwise, unless the one or more elements would make an embodiment or implementation non-functional, or unless two or more of the elements provide conflicting functions.

Aspects of the invention are described primarily in terms of an implementation using a da Vinci® Surgical System (specifically, a Model IS4000, marketed as the da Vinci® Xi™ HD™ Surgical System), commercialized by Intuitive Surgical, Inc. of Sunnyvale, Calif. Knowledgeable persons will understand, however, that inventive aspects disclosed herein may be embodied and implemented in various ways, including robotic and, if applicable, non-robotic embodiments and implementations. Implementations on da Vinci® Surgical Systems (e.g., the Model IS4000 da Vinci® Xi™ Surgical System, the Model IS3000 da Vinci Si® Surgical System) are merely exemplary and are not to be considered as limiting the scope of the inventive aspects disclosed herein.

The present disclosure describes a medical system that includes an image capture device for recording a medical procedure performed using the medical system. Additionally, the medical system includes a computer processor, and a memory device on which procedure event logs are stored. The procedure event logs record the occurrence of certain events taking place on the medical system. The procedure event logs further record the times at which these events took place. The medical system can synchronize the system events of the procedure event logs with corresponding medical procedure video recordings.

In one aspect, a user of a medical seeks to view a specific segment of recorded medical video that shows a specific portion of a medical procedure. The user inputs via a user interface one or more keywords that are descriptive of the subject matter shown in the sought after video segment. These inputs can be made using one of a variety of known input methods, such as through an external keyboard coupled to the medical system, through a touchscreen text entry interface of the medical system, or through a voice control interface of the medical system. A computer processor in data communication with the medical system uses information stored in the procedure event logs to identify one or more candidate video segments (or "video clips") of recorded medical video that are likely to include the subject matter of interest. This identification is possible because of known associations between (1) certain types of entries in the procedure event logs, and (2) certain medical events of interest (which are captured in the video recording of the medical procedure). Next, the computer algorithm applies to the candidate video clips (and not to any of the remaining video recording) an algorithm that analyzes at the image data contained in the frames of each of identified video clip, to determine whether any frames show the subject matter of interest being searched for. If the image data analysis algorithm affirmatively identifies one or more identified video clips as containing the subject matter of interest, then these video clips are presented to the user.

Minimally Invasive Teleoperated Surgical System

Referring now to the drawings, in which like reference numerals represent like parts throughout the several views, FIG. 1 is a plan view of a minimally invasive teleoperated surgical system 10, typically used for performing a minimally invasive diagnostic or medical procedure on a patient 12 who is lying on an operating table 14. The system includes a surgeon's console 16 for use by a surgeon 18 during the procedure. One or more assistants 20 may also participate in the procedure. The minimally invasive teleoperated surgical system 10 further includes a patient-side cart 22 and an electronics cart 24. The patient-side cart 22 can manipulate at least one removably coupled surgical instrument 26 through a minimally invasive incision in the body of the patient 12 while the surgeon 18 views the surgical site through the surgeon's console 16. An image of the surgical site can be obtained by an endoscope 28, such as a stereoscopic endoscope, which can be manipulated by the patient-side cart 22 to orient the endoscope 28. Computer processors located on the electronics cart 24 can be used to process the images of the surgical site for subsequent display to the surgeon 18 through the surgeon's console 16. The number of surgical instruments 26 used at one time will generally depend on the diagnostic or medical procedure and the space constraints within the operating room among other factors. If it is necessary to change one or more of the surgical instruments 26 being used during a procedure, an assistant 20 can remove the surgical instrument 26 from the patient-side cart 22, and replace it with another surgical instrument 26 from a tray 30 in the operating room.

Figure 2:
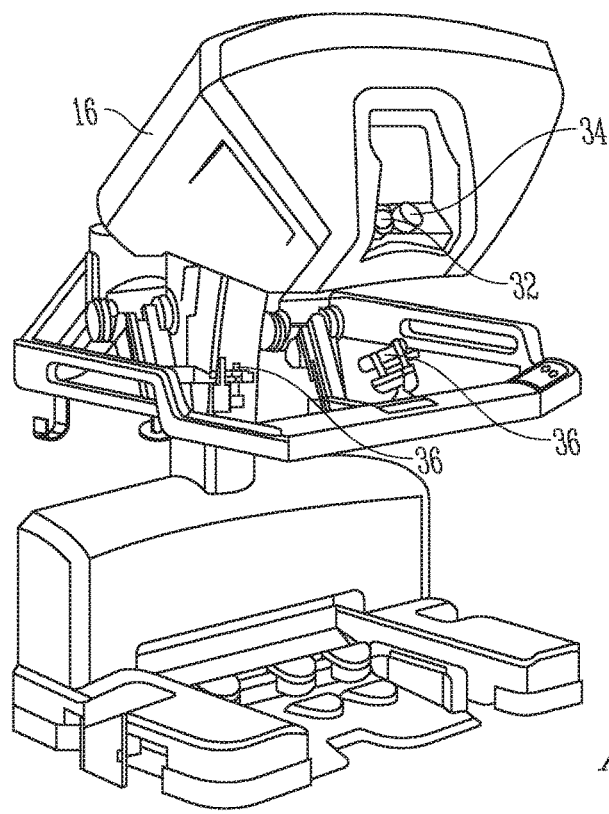
FIG. 2 is a perspective view of a surgeon's console.

FIG. 2 is a perspective view of the surgeon's console 16. The surgeon's console 16 includes a left eye display 32 and a right eye display 34 for presenting the surgeon 18 with a coordinated stereoscopic view of the surgical site that enables depth perception. The console 16 further includes one or more control inputs 36. One or more surgical instruments installed for use on the patient-side cart 22 (shown in FIG. 1) move in response to surgeon 18's manipulation of the one or more control inputs 36. The control inputs 36 can provide the same mechanical degrees of freedom as their associated surgical instruments 26 (shown in FIG. 1) to provide the surgeon 18 with telepresence, or the perception that the control inputs 36 are integral with the instruments 26 so that the surgeon has a strong sense of directly controlling the instruments 26. To this end, position, force, and tactile feedback sensors (not shown) may be employed to transmit position, force, and tactile sensations from the surgical instruments 26 back to the surgeon's hands through the control inputs 36.

The surgeon's console 16 is usually located in the same room as the patient so that the surgeon can directly monitor the procedure, be physically present if necessary, and speak to a patient-side assistant directly rather than over the telephone or other communication medium. But, the surgeon can be located in a different room, a completely different building, or other remote location from the patient allowing for remote medical procedures.

Figure 3:
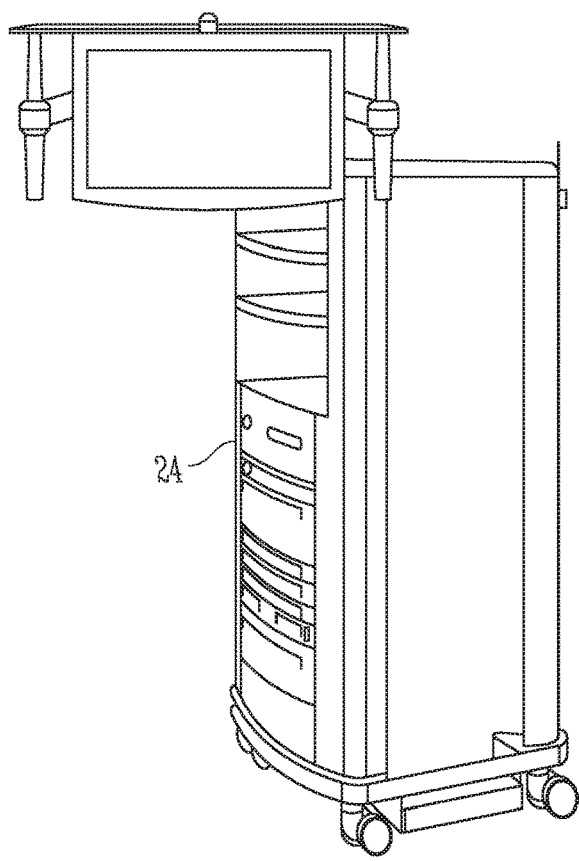
FIG. 3 is a perspective view of an electronics cart.

FIG. 3 is a perspective view of the electronics cart 24. The electronics cart 24 can be coupled with the endoscope 28 and includes a computer processor to process captured images for subsequent display, such as to a surgeon on the surgeon's console, or on another suitable display located locally and/or remotely. For example, if a stereoscopic endoscope is used, a computer processor on electronics cart 24 can process the captured images to present the surgeon with coordinated stereo images of the surgical site. Such coordination can include alignment between the opposing images and can include adjusting the stereo working distance of the stereoscopic endoscope. As another example, image processing can include the use of previously determined camera calibration parameters to compensate for imaging errors of the image capture device, such as optical aberrations. The captured images can also be stored onto a memory device for later viewing. Optionally, equipment in electronics cart may be integrated into the surgeon's console or the patient-side cart, or it may be distributed in various other locations in the operating room.

Figure 4:
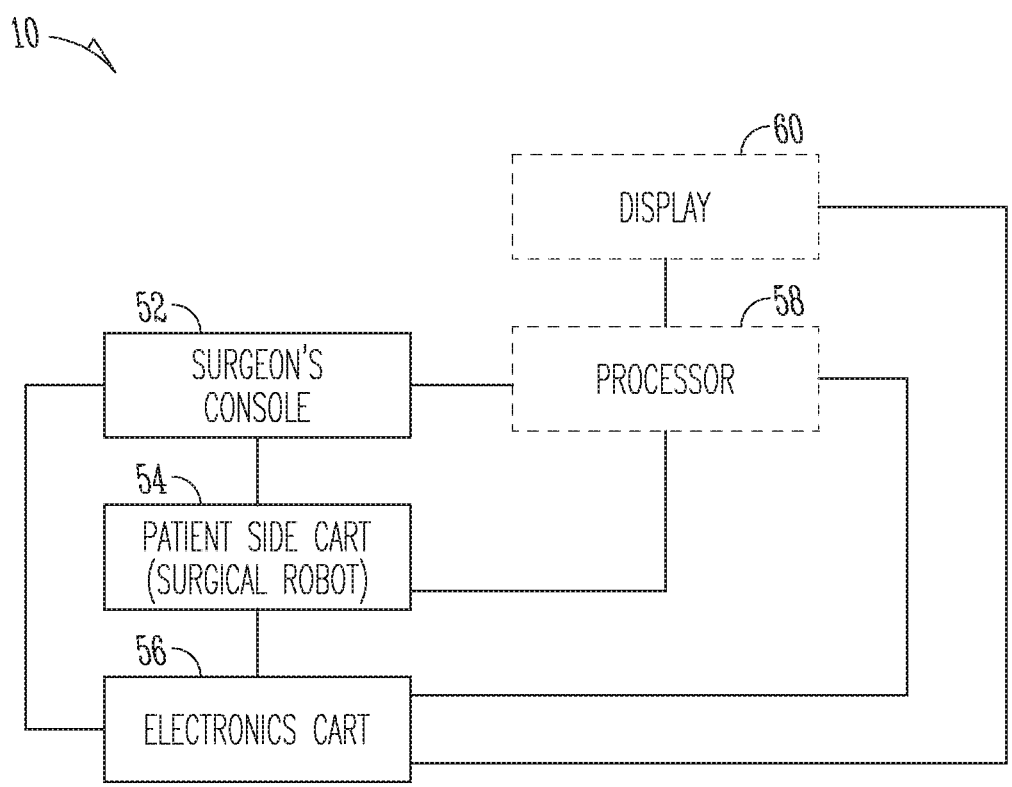
FIG. 4 is a diagrammatic illustration of a teleoperated surgical system.

FIG. 4 is a diagrammatic illustration of one embodiment of teleoperated surgical system 10. A surgeon's console 52 (such as surgeon's console 16 in FIG. 1) can be used by a surgeon to control a patient-side cart 54 (such as patent-side cart 22 in FIG. 1) during a minimally invasive procedure. The patient-side cart 54 can use an imaging device, such as a stereoscopic endoscope, to capture images of a surgical site and output the captured images to a computer processor located on an electronics cart 56 (such as the electronics cart 24 in FIG. 1). The computer processor typically includes one or more data algorithming boards purposed for executing computer readable code stored in a non-volatile memory device of the computer processor. The computer processor can process the captured images in a variety of ways prior to any subsequent display. For example, the computer processor can overlay the captured images with a virtual control interface prior to displaying the combined images to the surgeon via the surgeon's console 52.

Additionally or in the alternative, the captured images can undergo image processing by a computer processor located outside of electronics cart 56. In one embodiment, teleoperated surgical system 50 includes an optional a computer processor 58 (as indicated by dashed line) similar to the computer processor located on electronics cart 56, and patient-side cart 54 outputs the captured images to computer processor 58 for image processing prior to display on the surgeon's console 52. In another embodiment, captured images first undergo image processing by the computer processor on electronics cart 56 and then undergo additionally image processing by computer processor 58 prior to display on the surgeon's console 52. Teleoperated surgical system 50 can include an optional display 60, as indicated by dashed line. Display 60 is coupled with the computer processor located on the electronics cart 56 and with computer processor 58, and captured images processed by these computer processors can be displayed on display 60 in addition to being displayed on a display of the surgeon's console 52.

Figure 5:
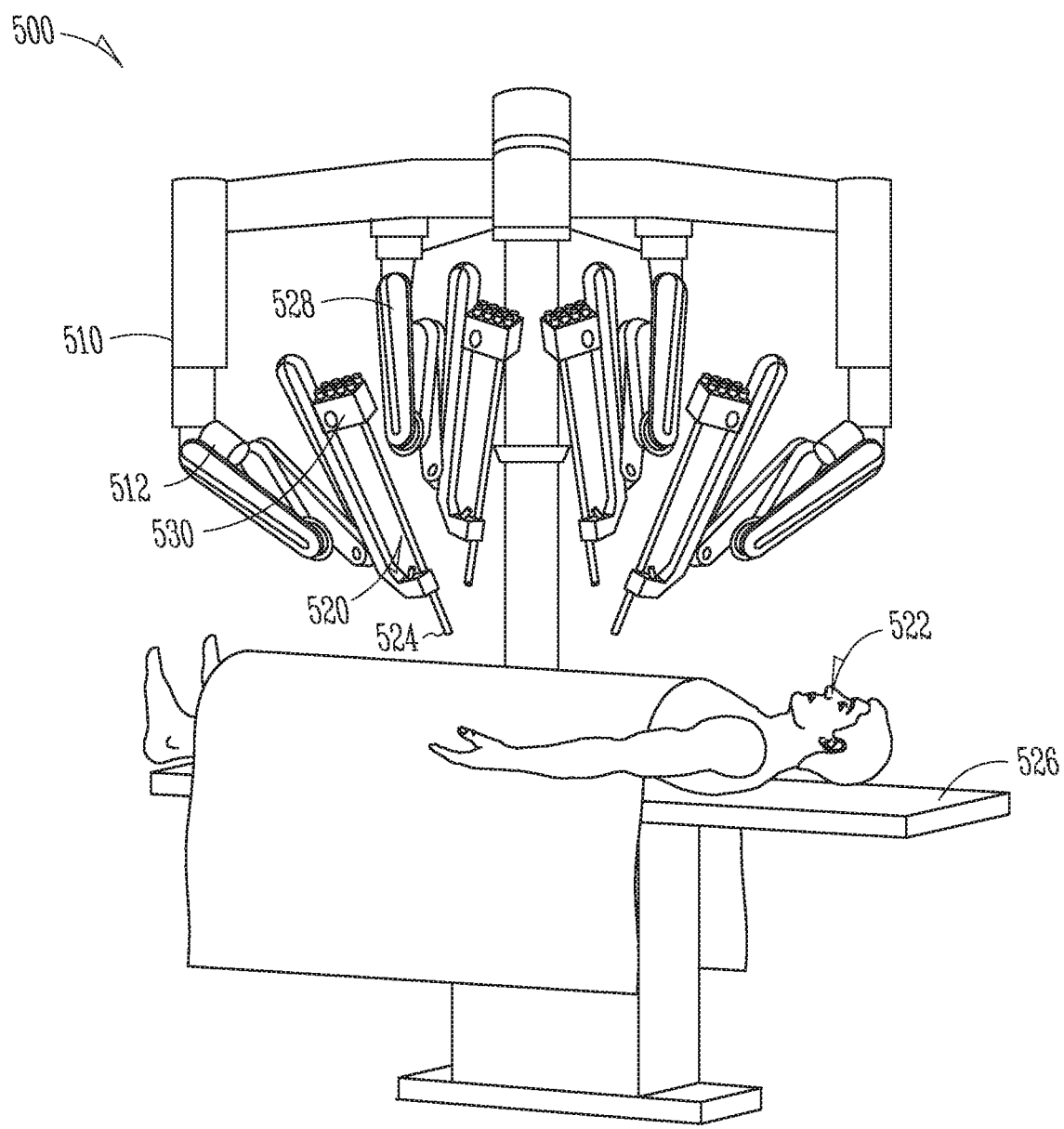
FIG. 5 is a perspective view of a patient-side cart.

FIG. 5 is a perspective view of a patient-side cart 500 of a minimally invasive teleoperated surgical system, in accordance with embodiments of the present invention. The patient-side cart 500 includes one or more support assemblies 510. A surgical instrument manipulator 512 is mounted at the end of each support assembly 510. Additionally, each support assembly 510 can optionally include one or more unpowered, lockable setup joints that are used to position the attached surgical instrument manipulator 512 with reference to the patient for surgery. As depicted, the patient-side cart 500 rests on the floor. In other embodiments, operative portions of the patient-side cart can be mounted to a wall, to the ceiling, to the operating table 526 that also supports the patient's body 522, or to other operating room equipment. Further, while the patient-side cart 500 is shown as including four surgical instrument manipulators 512, more or fewer surgical instrument manipulators 512 may be used.

A functional minimally invasive teleoperated surgical system will generally include a vision system portion that enables a user of the teleoperated surgical system to view the surgical site from outside the patient's body 522. The vision system typically includes a camera instrument 528 for capturing video images and one or more video displays for displaying the captured video images. Camera instrument 528 can be similar to endoscope 28 shown at FIG. 1. In some surgical system configurations, the camera instrument 528 includes optics that transfer the images from a distal end of the camera instrument 528 to one or more imaging sensors (e.g., CCD or CMOS sensors) outside of the patient's body 522. Alternatively, the imaging sensor(s) can be positioned at the distal end of the camera instrument 528, and the signals produced by the sensor(s) can be transmitted along a lead or wirelessly for processing and display on the one or more video displays. One example of a video display is the stereoscopic display on the surgeon's console in surgical systems commercialized by Intuitive Surgical, Inc., Sunnyvale, Calif.

Referring to FIG. 5, mounted to each surgical instrument manipulator 512 is a surgical instrument 520 that operates at a surgical site within the patient's body 522. Each surgical instrument manipulator 512 can be provided in a variety of forms that allow the associated surgical instrument to move with one or more mechanical degrees of freedom (e.g., all six Cartesian degrees of freedom, five or fewer Cartesian degrees of freedom, etc.). Typically, mechanical or control constraints restrict each manipulator 512 to move its associated surgical instrument around a center of motion on the instrument that stays stationary with reference to the patient, and this center of motion is typically located at the position where the instrument enters the body.

Surgical instruments 520 are controlled through computer-assisted teleoperation. A functional minimally invasive teleoperated surgical system includes a control input that receives inputs from a user of the teleoperated surgical system (e.g., a surgeon or other medical person). The control input is in communication with one or more computer-controlled teleoperated actuators, to which surgical instrument 520 is coupled. In this manner, the surgical instrument 520 moves in response to a medical person's movements of the control input. In one embodiment, one or more control inputs are included in a surgeon's console such as surgeon's console 16 shown at FIG. 2. A surgeon can manipulate control inputs 36 of surgeon's console 16 to operate teleoperated actuators of patient-side cart 500. The forces generated by the teleoperated actuators are transferred via drivetrain mechanisms, which transmit the forces from the teleoperated actuators to the surgical instrument 520.

Referring to FIG. 5, a surgical instrument 520 and a cannula 524 are removably coupled to manipulator 512, with the surgical instrument 520 inserted through the cannula 524. One or more teleoperated actuators of the manipulator 512 move the surgical instrument 512 as a whole. The manipulator 512 further includes an instrument carriage 530. The surgical instrument 520 is detachably connected to the instrument carriage 530. The instrument carriage 530 houses one or more teleoperated actuators that provide a number of controller motions that the surgical instrument 520 translates into a variety of movements of an end effector on the surgical instrument 520. Thus the teleoperated actuators in the instrument carriage 530 move only one or more components of the surgical instrument 520 rather than the instrument as a whole. Inputs to control either the instrument as a whole or the instrument's components are such that the input provided by a surgeon or other medical person to the control input (a "master" command) is translated into a corresponding action by the surgical instrument (a "slave" response).

Figure 6:
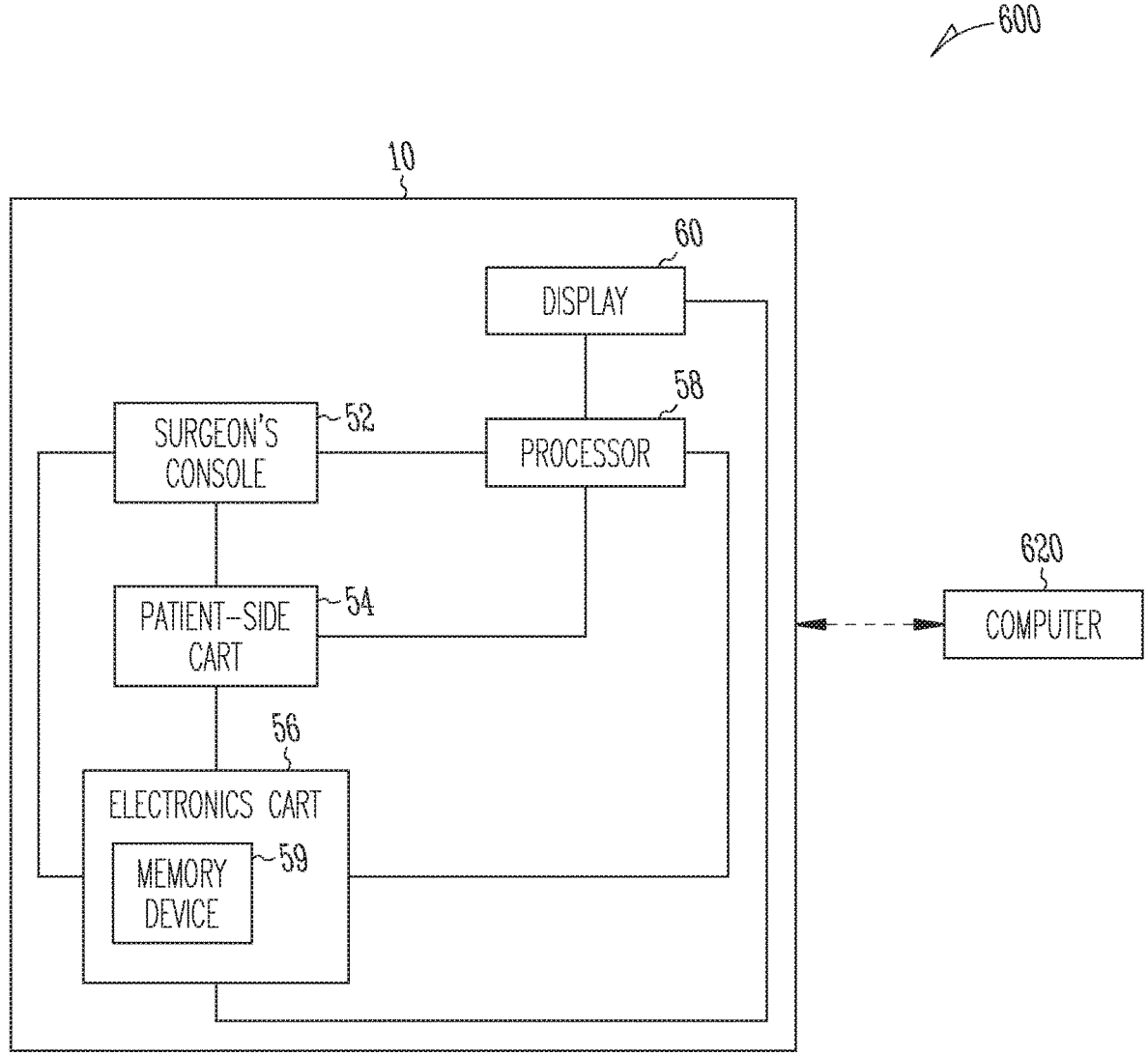
FIG. 6 is a diagrammatic illustration of a medical system.

FIG. 6 shows a schematic view of a medical system 600. Medical system 600 includes a teleoperated surgical system 10. As indicated by dashed line, medical system 600 can optionally include a computer 620 in data communication with teleoperated surgical system 10. In one embodiment, computer 620 is a personal computer. In alternate embodiments, computer 620 is a server or a mainframe. Data communication between computer 620 and teleoperated surgical system 10 can be via a variety of methods known in the art (e.g., an Local Area Network (LAN) connection, internet connection (wired or wireless), or similar data communication means). Additionally or in the alternative, this data communication can occur by means of data transfers from teleoperated surgical system 10 to computer 620 using a mobile hard drive or other similar data storage device. Computer 620 can be used to access information stored on a memory device of teleoperated surgical system 10, and the teleoperated surgical system 10 can be used to access information stored on a memory device of computer 620. A keyboard of computer 620 can provide a user interface for text entry. The text entered using the keyboard can be operated on by a computer processor of computer 620, as well as by a computer processor of teleoperated surgical system 10.

Medical system 600 includes a memory device on which one or more procedure event logs are maintained. FIG. 8 shows select portions of an exemplary procedure event log. In one embodiment, the memory device is memory device 59 located on electronics cart 56. In an alternate embodiment, the procedure event logs are maintained on a memory device located on surgeon's console 52. In yet another embodiment, the procedure event logs are maintained on a memory device located on computer 620.

The entries of the procedure event logs can include records of various interactions between teleoperated surgical system 10 and a medical person using teleoperated surgical system 10. In one embodiment, procedure event logs are automatically generated and automatically maintained in parallel with other operations performed by teleoperated surgical system 10 (e.g., computer-assisted teleoperation, video recording, video display, etc.). Input by a medical person is not required for the generation and maintenance of the procedure event logs of medical system 600.

Figure 7A:
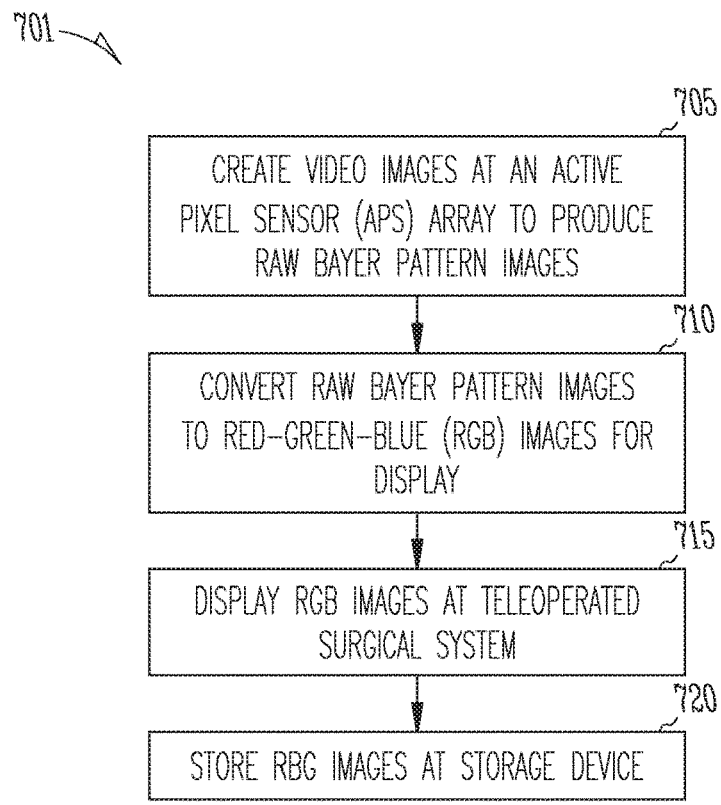
FIG. 7A is a flow diagram of an imaging algorithm of a medical system.
Figure 7B:
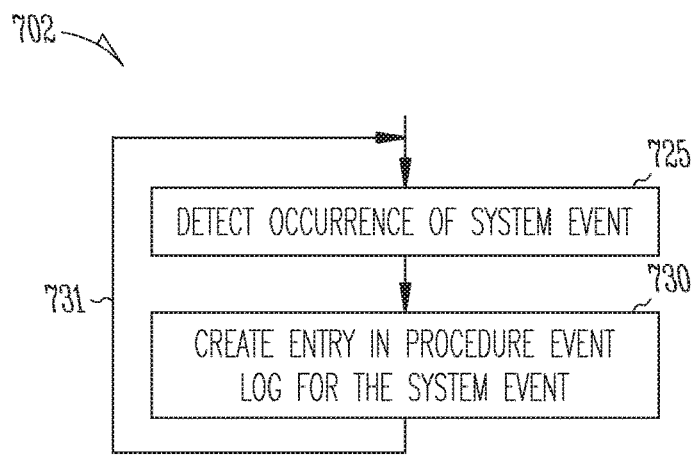
FIG. 7B is a flow diagram of an algorithm for creating an event log of a medical system.
Figure 7C:
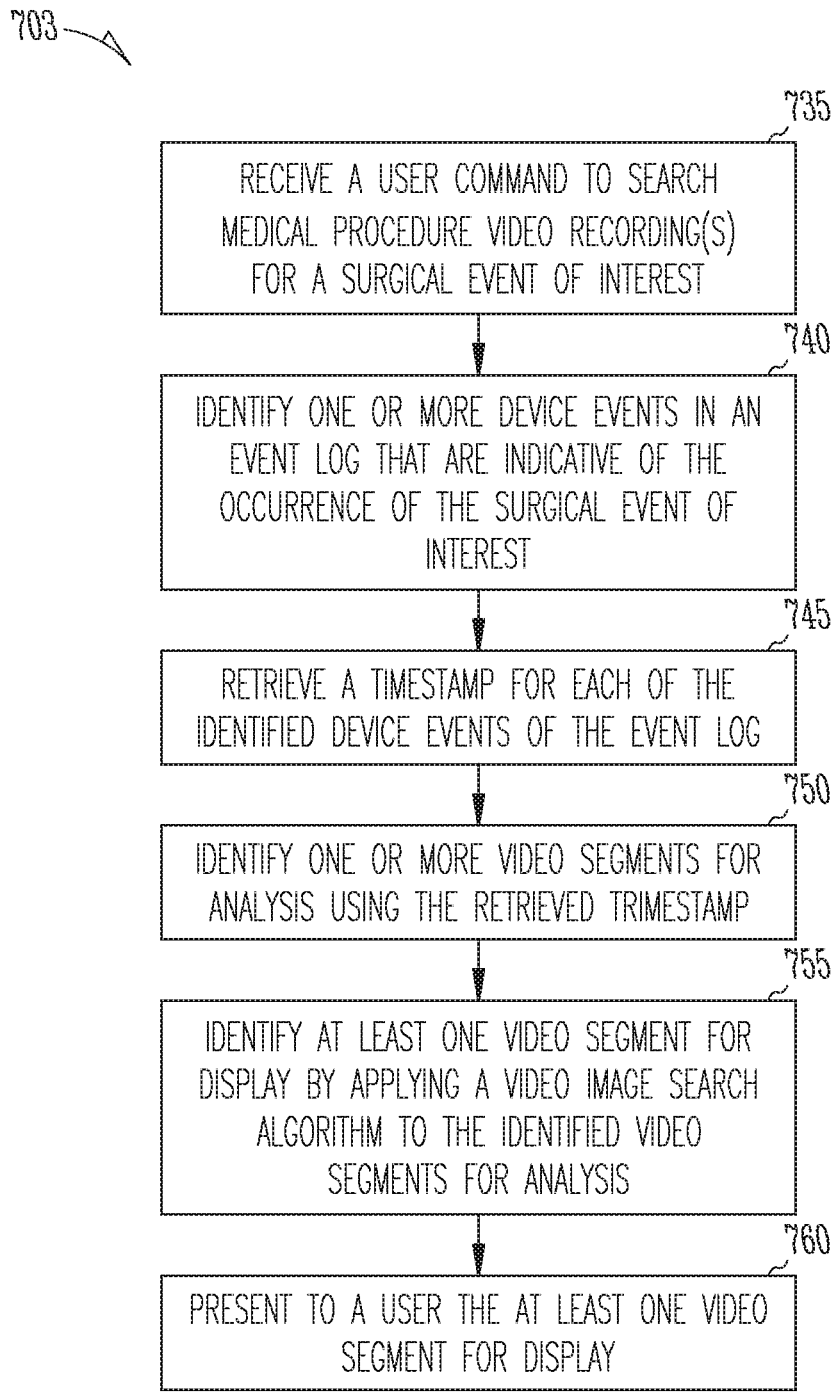
FIG. 7C is a flow diagram of an algorithm for using a medical system.

FIG. 7A is a flow diagram of an image capture and recording algorithm 701 of a medical system. FIG. 7B is a flow diagram of an algorithm that populates procedure event logs of the medical system in parallel with image capturing and recording. FIG. 7C is a flow diagram of an algorithm that: (1) uses the procedure event log data to identify one or more candidate video segments (or "video clips") of the captured video during which certain medical events of interest sought by a user of a device likely look place; and (2) applies to the candidate video clips (and not to any of the remaining video recording) an algorithm that looks at the image data contained in the frames of each of candidate video clip, to determine whether any frames show the medical events of interest that is sought after by a device user.

In one embodiment, algorithms 701, 702, and 703 are implemented by processor 58 of medical system 600 (shown at FIG. 6). In alternate embodiments, one or more of algorithms 701, 702, and 703 can be implemented by a processor other than processor 58.

Capturing, Processing, Displaying, and Storing Medical Video

FIG. 7A is a flow diagram showing an image capturing and recording algorithm 701 of a medical system. In one embodiment, the medical system includes a teleoperated surgical system. Referring to FIG. 7A, at 705, video images are captured by an image capture device. In one embodiment, the image capture device is an endoscope (e.g., endoscope 28 at FIG. 1) including an active pixel sensor (APS) array. The APS array is composed of red pixel sensors, green pixel sensors, and blue pixel sensors, which are arranged in a periodic pattern. Each pixel sensor of the APS array includes a photodetector and a light filter that limits the light frequencies to which the photodetector is exposed. The light filter of each red pixel sensor lets through only light that is in the red visible light portion of the electromagnetic (EM) radiation spectrum. Similarly, the light filter of each green pixel lets through only light that is in the green visible light portion of the EM spectrum, and the light filter of each blue pixel lets through only light that is in the blue visible light portion of the EM spectrum. Accordingly, each pixel sensor of the APS array will respond only to light that is within the EM spectrum range of its corresponding light filter. All other light frequencies that reach a pixel sensor are filtered out by its light filter and never reach its photodetector. Accordingly each pixel sensor of the APS array will generally have no response to light that is outside the EM spectrum range of its optical filter. A red pixel sensor will not respond to non-red light because the light filter of the red pixel sensor prevents all non-red light from reaching the red pixel sensor's photodetector. A green pixel sensor will not respond to non-green light because the light filter of the green pixel sensor prevents all non-green light from reaching the green pixel sensor's photodetector. And, a blue pixel sensor will not respond to non-blue light because the light filter of the blue pixel sensor prevents all non-blue light from reaching the blue pixel sensor's photodetector.

In one embodiment, the APS array described above is configured to produce raw bayer pattern images. Generally, each pixel of a raw bayer pattern image corresponds directly one-to-one to an individual pixel sensor of the APS array. As discussed previously, the APS array is composed of red pixel sensors, green pixel sensors, and blue pixel sensors, which are arranged in a periodic pattern. When the periodic arrangement of the various colored pixel sensors in the APS array is known, based on this color information, it is known what color each pixel of the raw bayer pattern image should be. If the pixel of the raw bayer pattern image corresponds to a red pixel sensor of the APS array, then the pixel should be red. If the pixel of the raw bayer pattern image corresponds to a green pixel sensor of the APS array, then the pixel should be green. If the pixel of the raw bayer pattern image corresponds to a blue pixel sensor of the APS array, then the pixel should be blue.

Pixel intensity is another piece of information needed to generate a raw bayer pattern image. This information is provided by the signals produced by the photoreceptor of each pixel sensor of the APS array. Consider for example a pixel of a raw bayer pattern image that corresponds with a red pixel sensor of the APS array. As discussed previously, the ability to determine that the pixel is associated with a red pixel sensor is based on prior knowledge of the periodic arrangement of the various colored pixel sensors of the APS array. The question, then, is whether this pixel of the raw bayer pattern image should be: (1) a faint red; or (2) a deep, saturated red. Whether this pixel is faint red or a deep, saturated red is determined by the amount of light that reaches the photoreceptor of the corresponding red pixel sensor of the APS array. As discussed previously, the light filter of the red pixel sensor blocks all non-red light, and allows only red light to pass through to the photoreceptor. Thus, whether this pixel is faint red or a deep, saturated red is determined by the amount of red light to which the red pixel sensor (or more precisely, its photoreceptor) is exposed. The more light that reaches a photoreceptor of a pixel sensor, the more intense the color of its corresponding pixel of a raw bayer pattern image. These principles apply similarly to green pixel sensors and blue pixels sensors of the APS array.

At 710, raw bayer pattern image data undergoes video processing to convert (1) raw bayer pattern images as captured by the endoscope, to (2) red-green-blue (RGB) images suitable for display. In one embodiment, this video processing at 710 involves a de-mosaicking processing module. Generally speaking, RGB images are based on an additive color model. The color of each pixel of an RGB image is determined by adding together an appropriate intensity of red color, green color, and blue color. Starting with a raw bayer pattern image, the de-mosaicking processing module creates an RGB image by adjusting the color of each red, green, or blue pixel of a raw bayer pattern image, using the information of different colored pixels that surround it. For example, a red pixel in a raw bayer pattern image is adjusted by augmenting it with color data from (1) one or more adjacent blue pixels, and (2) one or more adjacent green pixels. Using this method, the red pixel of the raw bayer pattern image is converted to an RGB image pixel with red, green, and blue color components. These principles apply similarly to the conversion of green pixels and blue pixels of the raw bayer pattern image to RGB image pixels.

One objective of the de-mosaicking processing module's image processing algorithms is to produce, through pixel-by-pixel adjustment, an RGB image in which each pixel of the RGB image is an accurate approximation of the ratio of red, green, and blue light that the corresponding pixel sensor of the APS array (i.e., of the endoscope) is exposed to. As discussed previously, each pixel sensor of the APS array includes a light filter, which lets through only red light if the pixel sensor is a red pixel sensor, only green light if it is a green pixel sensor, or only blue light if it is a blue pixel sensor. Non-red light that reaches a red pixel sensor is filtered out by the light filter of the red pixel sensor and never reaches the photodetector of the red pixel sensor. The same is true for non-green light that reaches a green pixel sensor, and for non-blue light that reaches a blue pixel sensor. Accordingly, the information detected by the photodetector of any single pixel sensor (whether red, green, or blue) corresponds exclusively to the intensity of a single color of light (i.e., the color of light allowed to pass through the particular light filter).

The APS array is made up of red pixel sensors, green pixel sensors, and blue pixel sensors, which are arranged in a periodic pattern. Generally, pixel sensors of different colors are not arranged adjacent to one another. For example, in one embodiment, each red pixel sensor is flanked by one or more green pixel sensors and one or more blue pixel sensors. One reason for this type of pixel sensor arrangement is to enable the de-mosaicking processing module's image processing algorithms to approximate one color component of the light reaching a particular pixel sensor using information from an adjacent pixel sensor. In one example, a red pixel sensor is flanked by a green pixel sensor to its left, a green pixel sensor to its right, a blue pixel sensor above, and a blue pixel sensor below. The red pixel sensor includes a light filter that allows through only red light through to the photodetector. All non-red light (e.g., green light, blue light, etc.) that reaches the pixel sensor is filtered out, and never reaches the photodetector. Accordingly, the signal from the photodetector of the red pixel sensor is an indication of the intensity of red light to which the red pixel sensor is exposed. The photodetector of the red pixel sensor, however, provides no information about the intensity of non-red light (e.g., green light or blue light) that reaches the red pixel sensor, because all non-red light is filtered out by the light filter of the red pixel sensor and never reaches the photodetector. In this example, however, two green pixel sensors and two blue pixel sensors surround the red pixel sensor. The photodetector of each of the two green pixel sensors provides information about the intensity of green light to which each green pixel sensor is exposed. The photodetector of each of the two blue pixel sensors provides information about the intensity of blue light to which each blue pixel sensor is exposed. This information from adjacent green pixel sensors and adjacent blue pixel sensors can be used to approximate the intensity of green light and blue light to which the red pixel sensor is exposed. This approximation of green light and blue light to which the red pixel sensor is exposed, together with information about red light intensity provided by the photodetector of the red pixel sensor, is used to generate an RGB image pixel corresponding to the red pixel sensor. The colors of RGB image pixels corresponding to green pixel sensors and blue pixel sensors can be determined in a similar manner.

Subsequent to video processing 710, the processed images are displayed at 715 to one or more users of a teleoperated surgical system (e.g., teleoperated surgical system 10 shown at FIG. 1). Referring to FIG. 1, these images can be displayed to a surgeon 18 seated at surgeon's console. Additionally, these images can be shown to other surgical staff on a display located on the electronics cart 24. In one embodiment, the processed images make up a SXGA video output at 60 frames per second (fps). Image data of the processed images is communicated over DVI-D connections to the various displays. In one embodiment, at 720, the processed images are additionally stored in a memory device. The processed images can be stored in their compressed and/or uncompressed format. In one embodiment, the processed images are stored on memory device 59 located on the electronics cart 56 (shown at FIG. 6). In an alternate embodiment, the processed images are stored on a memory device located on the surgeon's console 16 or the patient-side cart 22, or the storage device is a removable memory device (i.e., a "thumb drive") that is in data communication with the computer processor implementing the video processing at 720. Optionally, as indicated by dashed line at 706, un-processed raw bayer pattern image data generated at 705 can also be stored in this or another storage device.

In one embodiment, a sequence of images output by image processing at 710 is stored as a medical video at 720. A timestamp of the time at which the video recording began is embedded with the data of the medical video. Video recording can be commanded automatically when an image capture device (e.g., endoscope) is installed for use on a teleoperated surgical system. In alternate embodiments, video recording begins when a user initiates the recording. This timestamp can be used by a computer processor of a teleoperated surgical system configured to perform content searches of recorded medical video. This aspect will be discussed in greater detail below.

Populating Procedure Event Logs

Procedure event logs describing various system events occurring on a medical system (e.g., a portion of an exemplary event log is shown at FIG. 8) can be used to improve the speed and accuracy with which content searching can be performed on video recordings of medical procedures performed using the medical system. Namely, system events of procedure event logs that are of clinical significance can be used to identify video segments (i.e., "video slips") of medical procedure video recordings that are likely to contain certain content of interest.

In one embodiment, the medical system includes a teleoperated surgical system. Procedure event logs of the teleoperated surgical system are generally continuously maintained by a computer processor 58 (shown at FIG. 6) of the teleoperated surgical system, and stored on memory device 59 located on electronics cart 56 (shown at FIG. 6). In alternate embodiments, one or both the computer and the memory device can be located on another component of the teleoperated surgical system. The procedure event logs preferably includes entries for system events that include the following:

powering on/off the teleoperated surgical system
installation of an image capture device for use onto the teleoperated surgical system
initiation of video recording by a user of the teleoperated surgical system
installation of a surgical instrument onto the teleoperated surgical system
removal of a surgical instrument from the teleoperated surgical system
actuation of an electrocautery instrument functionality
adjusting the movement scaling between an input and an output of the teleoperated surgical system
turning on a special imaging mode of the teleoperated surgical system This list is by no means exhaustive. The event log can include entries corresponding to the occurrence of numerous other system events detectable by the teleoperated surgical system.

FIG. 7B is a flow diagram showing an algorithm 702 for automatically generating and maintaining procedure event logs of a medical system. Referring to FIG. 7B, at 725, algorithm 702 detects the occurrence of a system event. If the occurrence of a system event is detected at 725, then at 730, a corresponding entry is created in a procedure event log maintained on the medical system. Algorithm 702 updates the procedure event log by creating additional entries for each new system event that is detected, as indicated by 731. In one embodiment of the procedure event log, the following fields are recorded for each entry associated with the occurrence of a clinically system event: (1) a timestamp of the event; (2) a short description of the event; and (3) a unique code associated exclusively with the particular type of event. In one example, a surgical instrument (e.g., a needle driver instrument) is installed for use on the teleoperated surgical system (e.g., at 10:00 AM local time), which the teleoperated surgical system detects and identifies as a system event at 725. At 730, an associated entry is made and entered into a procedure event log. The short description field of the event log entry will read, "Needle Driver Instrument Installed". A unique code, e.g., 300006, that is associated with each installation of a needle driver instrument will be recorded also. Finally, a 10:00 AM timestamp for the entry is generated. The local time of the event can be determined locally on the teleoperated surgical system if it was previously programmed with the local time. Alternatively, if the teleoperated surgical system is connected to the internet, the local time of the event can be determined by performing an internet query, in which the internet protocol (IP) address associated with the teleoperated surgical system can be used to provide locational information.

Portions of a procedure event log having the data structure described above are shown at FIG. 8. As discussed previously, in one embodiment, the event log is automatically generated and automatically maintained with no input required, e.g., from a user of a medical system implementing algorithm 702. This generation and maintenance of the event log takes place in parallel to other operations of the medical system. These other operations of the medical system can include the video recording of a medical procedure performed using the medical system, as well as the video processing and storage of these medical procedure video recordings.

Searching the Captured Video

FIG. 7C is a flow diagram showing an algorithm 703 for searching recorded medical procedure video. Algorithm 703 makes use of the entries of a procedure event log. Referring to FIG. 7C, at 735, algorithm 703 receives a command issued by a user of the medical system to search recorded medical video for certain medical subject matter of interest. In one embodiment, the medical system includes a teleoperated surgical system. The user can issue this command by entering via a text entry interface certain text describing the medical event of interest, by speaking a certain phrase describing the medical event of interest through a voice-controlled user interface, or by other user interfaces known in the art. In one embodiment, this search is conducted intraoperatively by the operating surgeon (e.g., surgeon 18 at FIG. 1), and the search is limited to the recording of the instant medical procedure. In alternate embodiments, various medical procedure video recordings and their associated event logs are saved in a memory device. The contents of these saved medical procedure video recordings can be searched intraoperatively or postoperatively by a medical person. In one example, the medical person desiring to search the contents of these saved medical procedure video recordings issues the search command by entering via a keyboard (e.g., a keyboard of computer 620 shown at FIG. 6) certain text describing the medical event of interest.

At 740, algorithm 703 uses the information input at 735 to search one or more procedure event logs containing system events relating to the instant medical procedure, for one or more system events that are indicative of the occurrence of the medical event of interest. In one embodiment, 740 limits the event log search to the system events of the instant medical procedure by searching only the system events that follow the most recent powering on of the teleoperated surgical system. In alternate embodiments, 740 searches the system events of a collection of archived procedure event logs. Each archived procedure event log is associated with a medical procedure performed using the device, and in one embodiment, a video recording of associated medical procedure (procedure video recording) is archived with its corresponding procedure event log. In one embodiment, associations between (1) various medical events of interest, and (2) system events in the event log, are preprogrammed on a device implementing algorithm 703 when the device is manufactured. The information on which these algorithmic associations are based can be derived from the knowledge of medically trained persons with experience using the teleoperated surgical system. As more associations between medical events of interest and system events become known to the manufacturer of the device, an updated algorithm 703 incorporating these associations can be provided to teleoperated surgical systems in the field using an internet connection. These additional associations may be made by the manufacturer of the device after study of medical procedure video recordings and of event log data retrieved from examples of the teleoperated surgical system used in the field.

In accordance with the above discussion, in one example, at 735, a medical person using a teleoperated surgical system implementing algorithm 703 (e.g., surgeon 18 using teleoperated surgical system 10, both shown at FIG. 1) to perform a medical procedure wants to learn more about the circumstances surrounding an earlier part of the procedure, during which the patient experienced high blood loss. The medical person initiates a content search of a video recording of the instant medical procedure by speaking "high blood loss" into a voice-controlled search interface. The teleoperated surgical system is programmed to associate high blood loss with the use of an electrocautery instrument. Electrocautery instruments are commonly used to stop bleeding. At 740, algorithm 703 conducts a search on the portion of the event log corresponding to the instant medical procedure, for event log entries whose descriptions include "cautery" and "install". Referring to FIG. 8, in one example, the search at 740 produces a first system event 810, a second system event 820, and a third system event 830. These system events indicate three separate instances in which a cautery instrument was installed on the teleoperated surgical system. At 745, the timestamp for each of the search results generated by 740 is retrieved. In this example, the timestamps for the first system event 810, the second system event 820, and the third system event 830 are 10:00 AM, 11:00 AM, and 12:00 PM, respectively. At 750, a timespan of interest is determined for each of the retrieved timestamps. In the case of high blood loss, the teleoperated surgical system is programmed to identify as the timespan of interest a 3-minute video segment corresponding to each of the retrieved timestamps. Each 3-minute video segment begins one minute before each retrieved timestamp and continues for three minutes. These video segments are identified as candidate video clips. In this example, the three 3-minute video segments of interest (i.e., candidate video clips) are the following segments of the medical video: (1) the segment from 9:59 AM to 10:02 AM; (2) the segment from 10:59 AM to 11:02 AM; and (3) the segment from 11:59 AM to 12:02 AM. Different timespans of interest may be associated with different medical events of interest and with different system events.

At 755, an image search algorithm that analyzes image data is applied to the frames of the video segments of interest (i.e., the candidate video clips) identified at 750. In one embodiment, a first frame of each candidate video clip is located by determining the duration of time that has passed since video recording was initiated. As an example, with reference to FIG. 8, video recording was initiated at 805, which has a timestamp of 9:00 AM. 750 determined as the first candidate video clip the portion of the video recording taking place between 9:59 AM and 10:02 AM. Accordingly, the first frame of the first candidate video clip occurs at 59 minutes into the video recording. Similarly, the first frame of the second video segment of interest (the second candidate video clip) and of the third video segment of interest (the third candidate video clip) occur at 1 hour 59 minutes into the video recording and 2 hours and 59 minutes into the video recording, respectively. Likewise, the last frame of the first video segment of interest (the first candidate video clip), of the second video segment of interest (the second video clip), and the third video segment of interest occur (the third video clip) are at 1 hour 2 minutes, 2 hours 2 minutes, and 3 hours 2 minutes, respectively.

Discussion of an exemplary algorithm for determining the subject matter of an image using image data analysis can be found at U.S. Pat. No. 7,623,709 to Gering, entitled "Method and System for Segmenting Image Data" Generally, these algorithms look for certain patterns in the pixels of an image that are indicative of certain subject matter of interest. In this example, 755 is programmed to search the frames of the three candidate video clips identified above for pixel patterns that are indicative of high blood loss. In one embodiment, the image search algorithm positively identifies high blood loss when a sequence of frames making up a candidate video clip contain an increasing number of adjoining pixels of deep red color, as compared with the immediately preceding frame. In this example, 755 positively identifies high blood loss as being shown in the second candidate video clip (the video segment from 10:59 AM to 11:02 AM, corresponding to the second system event 820, shown at FIG. 8), and determines that high blood loss is not shown in the first candidate video clip (the 9:59 AM to 10:02 AM video segment, corresponding to the first system event 810, shown at FIG. 8) or in the third candidate video clip (the 11:59 AM to 12:02 PM video segment, corresponding to the third system event 830, shown at FIG. 8).

At 760, the candidate video clip identified at 755 (i.e., the video segment from 10:59 AM to 11:02 AM) is presented to the medical person for viewing. In one embodiment, this video segment is displayed automatically. In an alternate embodiment, a link is provided on a display for viewing by the medical person (e.g., on a display located on surgeon's console 16 shown at FIG. 1). The link is configured to play back to the medical person the portion of the recorded video corresponding to the identified video clip. Similarly, if more than one candidate video clip is identified at 755, more than one link can be displayed. Please note that the identified video clips and/or the one or more links configured to play back identified video clips can be presented to the medical person on any of a number of displays other than the display located on the surgeon's console 16. Additionally or in the alternative, this information can be displayed on a display associated with computer 620 (shown at FIG. 6).

In another example, 740 of the algorithm 703 includes analysis of the actuation frequency of a cautery function of an electrocautery instrument. Actuation of the cautery function can occur by way of a foot-activated pedal located on a surgeon's console of a teleoperated surgical system (e.g., surgeon's console 52 shown at FIG. 1). As discussed previously, cautery instruments are commonly used to stop bleeding. Generally, the more severe the bleeding, the more frequently the cautery functionality is actuated in the effort to stop the bleeding. In one embodiment, the teleoperated surgical system is programmed to associate high blood loss with the frequency with which the cautery function of an electrocautery instrument is actuated. In one example, a medical person viewing a medical procedure video recording seeks to learn more about the circumstances surrounding a part of the procedure during which the patient experienced high blood loss. The medical person initiates a video search in a manner similar to that discussed above. In this example, each actuation of the cautery function is a system event for which an entry is created in a procedure event log. At 740, algorithm 703 conducts a search of the procedure event log corresponding to the instant medical procedure, searching for procedure event log entries whose descriptions include "cautery" and "actuation". In one example, the search at 740 yields 30 entries. At 745, the timestamp for each of the search results generated by 1040 is retrieved. In this example: (1) the timestamp for the first entry is 10:00 AM; (2) the timestamps of entries 2-29 are closely spaced and span the period between 11:00 AM and 11:02 AM; and (3) the timestamp for entry 30 is 12:00 PM. At 750, a timespan of interest is determined using the timestamps retrieved at 745. In this example, the teleoperated surgical system is programmed to identify as the timespan of interest a 3-minute video segment (i.e., candidate video clip) corresponding to instances in which the cautery function is actuated more than 10 times in a 2 minute period. Each candidate video clip begins one minute before the timestamp of the event log entry corresponding to the first cautery actuation in the sequence of cautery actuations, and continues for two minutes after that timestamp. In this example, the frequency of cautery actuation between 11:00 AM and 11:02 AM is the only instance satisfying the more-than-10-times-in-2-minutes test. Accordingly, only one candidate video clip is identified: the segment from 10:59 AM to 11:02 AM. 755 and 760 operate in a manner similar to that described previously.

In another example, a medical person using a teleoperated surgical system implementing algorithm 703 (e.g., surgeon 18 using teleoperated surgical system 10, both shown at FIG. 1) to perform a cholecystectomy wants to learn more about the circumstances surrounding the mobilization of the gallbladder from the duodenum wall during the procedure. The medical person initiates a content search of a video recording of the cholecystectomy procedure by speaking "gallbladder mobilization" into a voice-controlled search interface. The teleoperated surgical system is programmed to associate gallbladder mobilization (a medical event of interest) with the use of a fluorescence imaging mode (a system event logged in procedure event logs). Fluorescence imaging is frequently used to improve visualization of certain anatomy during the gallbladder mobilization portion of a cholecystectomy. Accordingly, at 740, algorithm 703 conducts a search on the portion of the event log corresponding to the instant cholecystectomy procedure, searching for event log entries whose descriptions include "fluorescence" and "on". In one example, the search at 740 yields a first entry, a second entry, and a third entry. At 745, the timestamp for each of the search results generated by 740 is retrieved. In this example, the timestamps for the first entry, the second entry, and the third entry are 10:00 AM, 11:00 AM, and 12:00 PM, respectively. At 750, a timespan of interest is determined for each of the retrieved timestamps. In the case of gallbladder mobilization, the teleoperated surgical system is programmed to identify as the timespan of interest a 10-minute video segment corresponding to each of the retrieved timestamps. Each 10-minute video segment begins at the time of the retrieved timestamp and continues for ten minutes after the timestamp. In this example, the three 10-minute video segments of interest (candidate video clips) are the following segments of the medical video: (1) the segment from 10:00 AM to 10:10 AM; (2) the segment from 11:00 AM to 11:10 AM; and (3) the segment from 12:00 PM to 12:10 PM. 755 and 760 operate in a manner similar to that described previously.

In another example, a medical person using a teleoperated surgical system implementing algorithm 703 (e.g., surgeon 18 using teleoperated surgical system 10, both shown at FIG. 1) to perform a mitral valve repair procedure wants to learn more about the circumstances surrounding the reconstructive work performed during a mitral valve repair procedure. The medical person initiates a content search of a video recording of the mitral valve repair procedure by speaking "valve reconstruction" into a voice-controlled search interface. The teleoperated surgical system is programmed to associate valve reconstruction (a medical event of interest) with the use of a fine control mode (a system event logged in procedure event logs). In contrast to the coarse control mode, the fine control mode affords the user of the teleoperated surgical system the ability to command smaller movements of the surgical instruments. As discussed previously, in one embodiment of a teleoperated surgical system, surgical instruments coupled to slave robotic manipulators move in response to a surgeon's movement of two control inputs located on a surgeon's console. In a coarse control mode, a surgical instrument may move 5 mm in response to a surgeon's movement of a control input by 1 cm. In a fine control mode, the same movement 1 cm movement of the control input may produce only a 2.5 mm movement of the surgical instrument. A fine control mode is frequently used by a surgeon who is operating in areas of delicate anatomy. Compared to the coarse control mode, the finer scaling between (1) the movement of the control input, and (2) the movement of a corresponding surgical instrument, enables the surgeon to make smaller dissections and smaller sutures.

Accordingly, at 740, algorithm 703 conducts a search on the portion of the event log corresponding to the instant valve repair procedure, searching for event log entries whose descriptions include "fine control mode". In one example, the search at 740 yields a first entry, a second entry, and a third entry. At 745, the timestamp for each of the search results generated by 740 is retrieved. In this example, the timestamps for the first entry, the second entry, and the third entry are 10:00 AM, 11:00 AM, and 12:00 PM, respectively. At 750, a timespan of interest is determined for each of the retrieved timestamps. In the case of valve reconstruction, the teleoperated surgical system is programmed to identify as the timespan of interest a 30-minute video segment corresponding to each of the retrieved timestamps. Each 30-minute video segment begins at the time of the retrieved timestamp and continues for 30 minutes after the timestamp. In this example, the three 30-minute video segments of interest (i.e., candidate video clips) are the following segments of the medical video: (1) the segment from 10:00 AM to 10:30 AM; (2) the segment from 11:00 AM to 11:30 AM; and (3) the segment from 12:00 PM to 12:30 PM. 755 and 760 operate in a manner similar to that described previously.

For each of the preceding examples, the candidate video clips are evaluated to determine, using the image data of each of the candidate video clips, whether the pixels of the frames making up each candidate video clip are actually indicative of the subject matter of interest desired by the user. Candidate video clips for which this determination is made in the affirmative are presented to a user for viewing.

Figure 9:
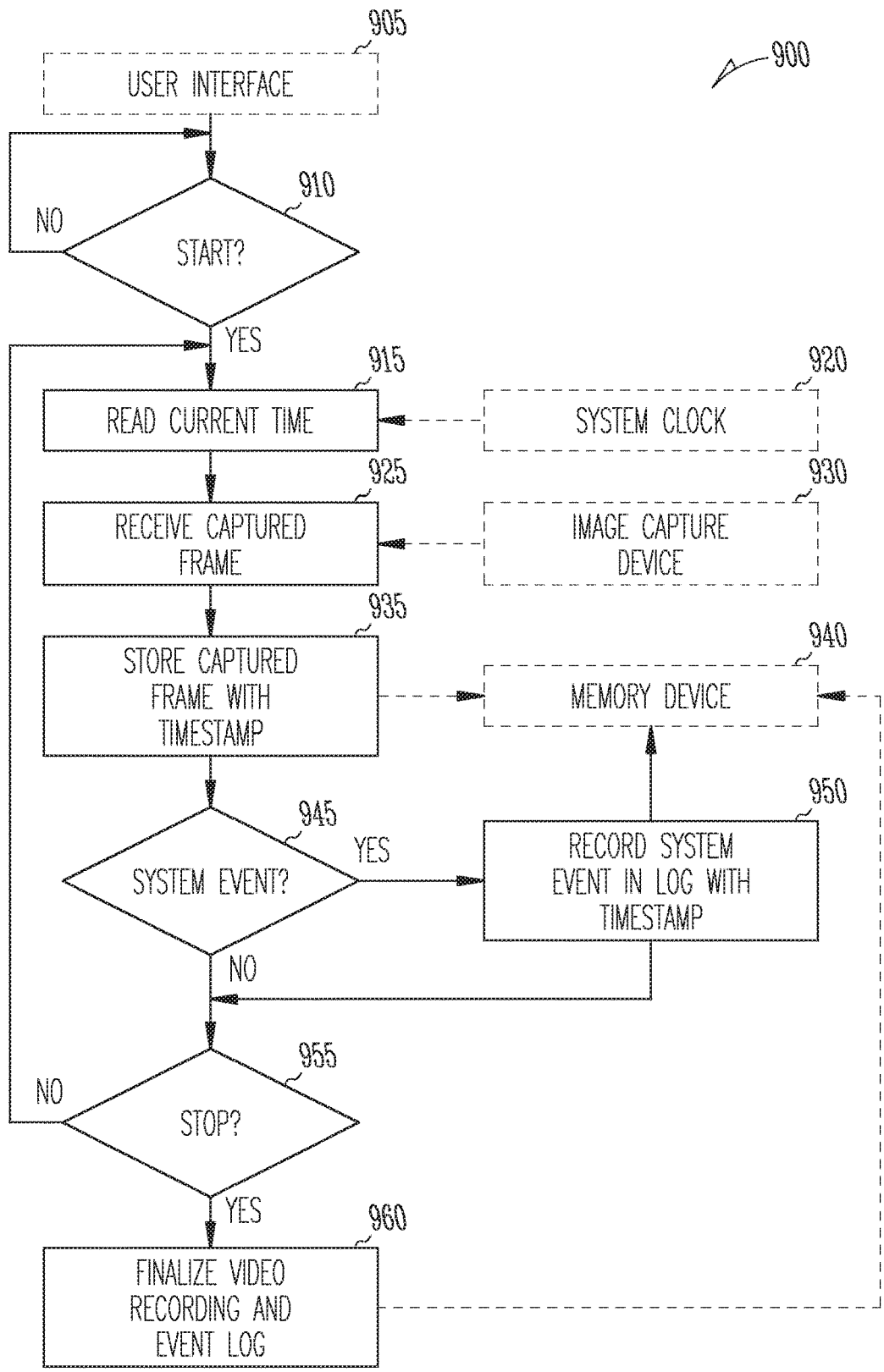
FIG. 9 is a flow diagram of a data library maintenance algorithm.

FIG. 9 shows a flow diagram of algorithm 900, which directs the data collection for and maintenance of a data library of a device. In one embodiment, the device is a teleoperated surgical system, and the data library includes: (1) one or more video recordings (procedure video recordings) of surgical procedures performed using the surgical system; and (2) a procedure event log for each of the one or more procedure video recordings. The data library can be stored on a memory device of the teleoperated surgical system. Additionally or in the alternative, the data library can be stored: (1) in a memory device located on a remote server in data communication with the teleoperated surgical system; (2) in the memory of a cloud computing system that is in data communication with the teleoperated surgical system; or (3) any other electronic storage medium option.

In one embodiment, every time the surgical system is powered on, a new procedure event log is created. In one instance, powering on the surgical system creates a new procedure event log, but does not start the recording of video captured by an image capture device associated with the surgical system; a user is required to make an input via a user interface of the surgical system to start recording video captured by the image capture. In another instance, if an image capture device (e.g., an endoscope) is installed on the surgical system when the surgical system is powered on, then the powering on of the surgical can additionally cause the surgical system to begin recording video captured by the image capture device. In another instance, recording of video captured by an image capture device is initiated automatically when the image capture device is installed for use onto a surgical system that is already powered on. These examples are merely exemplary, and not intended to be limiting.

As shown in FIG. 9, algorithm 900 is initiated when it receives a START signal at 910. The START signal is the product of a user's input received via user interface 905 (e.g., actuating a power on/off switch). If the START signal is not received, then algorithm 900 loops back and repeats the query at 910.

If the START signal is received at 910, algorithm 900 proceeds to 915, at which algorithm 900 queries a system clock 920 to read the current time. At 925, algorithm 900 receives an image from an image capture device 930 in data communication with a computer processor executing algorithm 900, the image being one frame of a video recording captured by the image captured device 930. At 935, the image received at 925 is digitally timestamped with the current time read at 915, and the timestamped image is saved to a memory device 940 as one frame of a video recording.

Algorithm 900 also updates and maintains a procedure event log. As discussed previously, in one embodiment, a procedure event log is created each time the device performing algorithm 900 (e.g., a teleoperated surgical system) is powered on. At 945, algorithm 900 queries the surgical system to determine whether one of a number of system events of interest is detected at that moment. Preferably, a memory device of the surgical system includes a look-up table containing a pre-identified list of system events to be logged in procedure event logs. If 945 detects the occurrence of one of the system events contained in the look-up table, the identified system event is retrieved and, at 950, digitally timestamped with the current time determined at 915. This system event and its associated timestamp are saved to memory device 840 as an entry in the procedure event log. Algorithm 900 then proceeds to 955, which will be discussed in greater detail below.

If 945 determines that none of the system events contained in the look-up table are taking place, algorithm 900 proceeds directly to 955, at which algorithm 900 queries whether a STOP signal has been received. If the STOP signal is received, algorithm 900 will stop video recording and will discontinue updates to the procedure event log for the existing surgical procedure. Preferably, the STOP signal is the product of a user input via a user interface (e.g., user interface 905). In one embodiment, the STOP signal is received when the system is powered off (e.g., when a user actuates a power on/off switch). These examples are merely exemplary, and not intended to be limiting.

If a STOP signal is received, algorithm 900 proceeds to 960, at which the images making up the various frames of the procedure video recording are compiled to produce a viewable video recording, and the various system events making up the entries of the procedure event log are compiled to form a complete procedure event log. The compiled procedure video recording and the procedure event log are then saved to memory device 940, for later use. If a STOP signal is not received, algorithm 900 loops back to run 915 again.

Figure 10:
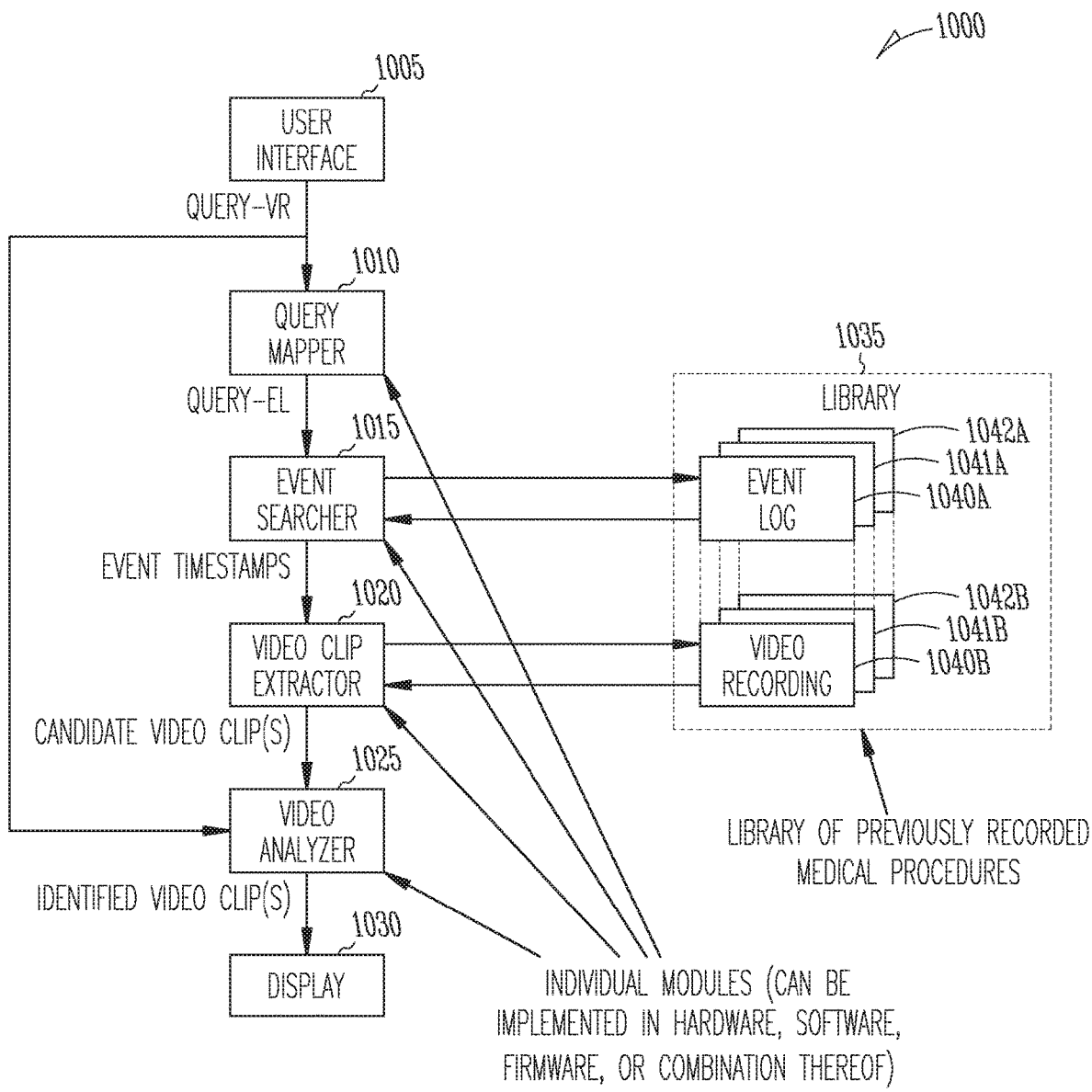
FIG. 10 is a flow diagram of an algorithm for searching the content of video.

FIG. 10 shows an algorithm 1000 that performs video content searches using a combination of image data and auxiliary data. In one application, algorithm 1000 can be used to search various procedure video recordings (e.g., procedure video recordings generated by algorithm 900, shown at FIG. 9) for certain subject matter of interest. In this application, the data contained in the procedure event logs, each of which is associated with a particular procedure video recording, constitutes auxiliary data that can be used to facilitate a search of the procedure video recordings for certain subject matter of interest. Algorithm 1000 can be carried out by a computer processor of the device carrying out algorithm 900 (e.g., a computer processor that is part of a teleoperated surgical system). Algorithm 1000 can also be carried out by a computer processor in data communication with the device carrying out algorithm 900 (e.g., a personal computing device).

In one embodiment, algorithm 1000 makes use of known associations between (1) specific system events logged in the procedure event log, and (2) specific medical subject matter of interest, to facilitate a user's search for portions of procedure video recordings containing the specific medical subject matter of interest. As discussed previously, this approach of algorithm 1000 improves upon various shortcomings associated with earlier video search algorithms that rely exclusively on image data analysis.

Referring to FIG. 10, in one embodiment, algorithm 1000 is initiated by a user request commanded via user interface 1005. At user interface 1005, a user requests that certain procedure video recordings be searched for certain subject matter of interest to the user. In one example, the user is a surgeon preparing to perform a particular surgical procedure involving a specific surgical technique, and the surgeon would like to view portions of archived procedure video recordings showing that specific surgical technique. User interface 1005 may be a microphone, using which the user can command a search of previously recorded video for certain subject matter of interest. Alternatively, the user interface might be a touchpad or some alternate user interface that provides text entry means. These examples are merely exemplary, and not intended to be limiting.

In one embodiment, at 1010, a query mapper associates one or more terms contained in the user search requested at 1005 with one of the system events ordinarily recorded by the procedure event logs. Preferably, query mapper 1010 operates by searching a look-up table containing known associations between (1) various key terms or phrases, and (2) individual system events or patterns of several system events. As additionally associations become known, this look-up table can be updated to reflect the additional associations.

In one example, a user requests at 1005 to search procedure video recordings for surgical techniques to mitigate patient bleeding during a surgical procedure. The query mapper at 1010 operates on this user query, and determines that system events that indicate frequent applications of an electrocautery functionality associated with cautery instruments during a given surgical procedure correspond to a common surgical technique used to mitigate patient bleeding. Continuing with this example, at 1015, event searcher searches procedure event logs archived in a data library 1035 for repeated applications of electrocautery in a given period (e.g., at least 10 applications of electrocautery energy in a 1-minute time span).

Referring to FIG. 10, exemplary data library 1035 shows procedure event logs 1040a,1041a,1041a. Each of procedure event logs 1040a,1041a, 1042a is associated with one of the procedure video recordings 1040b,1041b,1042b. Continuing with the above example, event searcher 1015 searches through procedure event logs 1040a,1041a,1042a for instances repeated applications of electrocautery in a given period, and finds that only procedure event log 1040a and procedure event log 1041a contain periods that satisfy the specified frequency of electrocautery application.

As discussed previously with respect to algorithm 900, in one embodiment, each system event of a procedure event log (e.g., procedure event log 1040a,1041a,1042a) is archived with a corresponding timestamp and each frame of a procedure video recording (e.g., procedure video recording 1040a,1041a,1042a) is archived with a corresponding timestamp. Video clip extractor 1020 operates on the output of event searcher 1015 by using one or more timestamps associated with system events of a procedure event log to retrieve a corresponding segment of the procedure video recording. Continuing with the above example, using the output of event searcher 1015, video clip extractor 1020 retrieves from procedure video recordings 1040b,1041b a candidate video clip for each of the portions of procedure event logs 1040a,1041a that satisfy the specified frequency of electrocautery application.

Each of the candidate video clips retrieved by video clip extractor 1020 is submitted for analysis to video analyzer 1025 for analysis. Video analyzer 1025 analyzes the image data corresponding to each of the candidate video clips to determine whether each of the candidate video clips actually contains the subject matter of interest sought by the user. Continuing with the above example, video analyzer 1025 determines that only one candidate video clip from procedure video recording 1040b actually contains the subject matter of interest sought by the user, and identifies this candidate video clip as an identified video clip. At 1030, this identified video clip is presented to the user for viewing.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the disclosure should be limited only by the following claims, and it is appropriate that the claims be construed broadly and in a manner consistent with the scope of the embodiments disclosed herein.

We claim:

1. A method comprising:
   receiving a user command that includes a user description of a medical procedure event of interest, to locate one or more video clips showing the medical procedure event of interest, that is a portion of a medical procedure performed on a medical system, from one or more medical procedure video recordings of the medical procedure;
   identifying, from one or more medical system event logs that associate medical system events with user descriptions of medical procedure events, that each is associated with one or more medical procedure video recordings having timestamped frames, that each records occurrences of medical system events, during performance of medical procedures on the medical system, and that each records times of occurrence of medical system events on the medical system, one or more medical system events occurring on the medical system during the medical procedure that correspond to the occurrence of the medical procedure event of interest;

identifying one or more candidate video clips from the one or more medical procedure video recordings having timespans corresponding to timestamps of one or more frames that correspond to the medical procedure of interest and that correspond to one or more timestamps corresponding to each of the one or more identified medical system events occurring on the medical system;

determining, by searching the image data of the one or more candidate video clips for patterns in pixels that are indicative of the medical procedure event of interest, whether each of the one or more candidate video segments is an identified video segment that contains the medical procedure event of interest; and presenting to a user at least one identified video segment.

2. The method of claim 1, wherein receiving the user command to locate one or more video clips showing a medical event of interest comprises:

presenting a plurality of video clips of medical procedure events of interest to choose from via a user interface;

receiving a user's selection of one of the presented plurality of video clips of medical procedure events of interest.

3. The method of claim 1, wherein receiving a user command to locate one or more video clips showing a medical event of interest comprises receiving the user command intraoperatively while the user is performing a medical procedure.

4. The method of claim 1, wherein receiving a user command to locate one or more video clips showing a medical event of interest comprises receiving the user command preoperatively or postoperatively.

5. The method of claim 1, wherein identifying one or more system events that correspond to the occurrence of the medical event of interest comprises searching a look-up table that records the occurrence of events and the time of occurrence of medical system events on the medical system.

6. The method of claim 5, wherein the look-up table is periodically updated automatically to account for associations between medical system events and medical events of interest learned through machine learning.

7. The method of claim 1, wherein the one or more medical system events that correspond to the occurrence of the medical event of interest comprises the occurrence of an individual system event.

8. The method of claim 1, wherein the one or more medical system events that correspond to the occurrence of the medical event of interest comprises occurrence of two or more system events accordingly to a particular pattern.

9. The method of claim 1, wherein the one or more medical system events that correspond to the occurrence of the medical event of interest comprises the occurrence of an individual system event for a prolonged duration.

10. The method of claim 1, wherein identifying one or more candidate video segments for one or more timestamps corresponding to each of the one or more identified medical system events comprises identifying a video segment of a procedure video recording taking place between two timestamps.

11. The method of claim 1, wherein identifying one or more candidate video segments for one or more timestamps corresponding to each of the one or more identified medical system events comprises identifying a video segment of a procedure video recording taking place within a time window of a timestamp.

12. The method of claim 1, wherein presenting to the user at least one identified video segment comprises playing to the user the at least one identified video segment on a display.

13. A device for performing a video search, comprising:

a user interface; and a processing unit operatively coupled to the user interface, the processing unit including one or more processors, wherein the processing unit is configured to:

receiving, via the user interface, a user command that includes a user description of a medical procedure event of interest, to locate one or more video clips showing a medical procedure event of interest, that is a portion of a medical procedure performed on a medical system, from one or more medical procedure video recordings of the medical procedure;

identifying, from one or more medical system event logs that associate medical system events with user descriptions of medical procedure events, that each is associated with one or more medical procedure video recordings having timestamped frames, that each records occurrences of medical system events, during performance of medical procedures on the medical system, and that each records times of occurrence of medical system events on the medical system, one or more medical system events occurring on the medical system during the medical procedure that correspond to the occurrence of the medical procedure event of interest;

identifying one or more candidate video clips from the one or more medical procedure video recordings having timespans corresponding to timestamps of one or more frames that correspond to the medical procedure of interest and that correspond to one or more timestamps corresponding to each of the one or more identified medical system events occurring on the medical system;

determining, by searching the image data of the one or more candidate video clips for patterns in pixels that are indicative of the medical procedure event of interest, whether each of the one or more candidate video segments is an identified video segment that contains the medical procedure event of interest; and presenting to a user at least one identified video segment.

14. The device of claim 13, wherein the user interface comprises a user interface of a personal computing device.

15. The device of claim 13, wherein the user interface comprises a user interface of a teleoperated surgical system.

16. The device of claim 13, wherein receiving the user command to locate one or more video clips showing a medical procedure event of interest comprises:

presenting a plurality of video clips of medical procedure events of interest to choose from via a user interface;

receiving a user's selection of one of the presented plurality of medical procedure events of interest.

17. The device of claim 13, wherein identifying one or more medical system events that correspond to the occurrence of the medical procedure event of interest comprises searching a look-up table that records the occurrence of events and the time of occurrence of medical system events on the medical system.

18. The device of claim 17, wherein the look-up table is periodically updated automatically to account for associations between medical system events and medical procedure events of interest learned through machine learning.

19. The device of claim 13, wherein the one or more medical system events likely to correspond to the occurrence of the medical procedure event of interest comprises the occurrence of an individual medical system event.

20. The device of claim 13, wherein the one or more medical system events likely to correspond to the occurrence of the medical procedure event of interest comprises occurrence of two or more system events accordingly to a particular pattern.

21. The device of claim 13, wherein the one or more medical system events likely to correspond to the occurrence of the medical procedure event of interest comprises the occurrence of an individual medical system event for a prolonged duration.

22. The device of claim 13, wherein identifying one or more candidate video segments for one or more timestamps corresponding to each of the one or more identified medical system events comprises identifying a video segment of a medical procedure video recording taking place between two timestamps.

23. The device of claim 13, wherein identifying one or more candidate video segments for one or more timestamps corresponding to each of the one or more identified medical system system events comprises identifying a video segment of a medical procedure video recording taking place within a time window of a timestamp.

24. The device of claim 13, wherein presenting to the user at least one identified video segment comprises playing to the user the at least one identified video segment on a display.

* * * * *

UNITED STATES PATENT AND TRADEMARK OFFICE
CERTIFICATE OF CORRECTION

PATENT NO. : 10,600,510 B2
APPLICATION NO. : 15/735073
DATED : March 24, 2020
INVENTOR(S) : Mohr et al.

Page 1 of 1

It is certified that error appears in the above-identified patent and that said Letters Patent is hereby corrected as shown below:

On the Title Page

In item (22), in "PCT Filed", in Column 1, Line 1, delete "Jun. 9, 2016" and insert --Jun. 8, 2016-- therefor In item (60), in "Related U.S. Application Data", in Column 1, Lines 1-2, delete "Jun. 19, 2015." and insert --Jun. 9, 2016-- therefor In the Claims In Column 23, Line 22, in Claim 23, delete "system system" and insert --system-- therefor Signed and Sealed this
Nineteenth Day of May, 2020

Andrei Iancu
*Director of the United States Patent and Trademark Office*